(12) United States Patent
Chobotov et al.

(10) Patent No.: US 12,350,142 B2
(45) Date of Patent: Jul. 8, 2025

(54) SYSTEMS AND METHODS WITH GRAFT BODY, INFLATABLE FILL CHANNEL, AND FILLING STRUCTURE

(71) Applicant: Endologix LLC, Irvine, CA (US)

(72) Inventors: Michael Chobotov, Irvine, CA (US); James Machek, Irvine, CA (US); David Deaton, Irvine, CA (US); William Colone, Irvine, CA (US)

(73) Assignee: Endologix LLC, Irvine, CA (US)

( * ) Notice: Subject to any disclaimer, the term of this patent is extended or adjusted under 35 U.S.C. 154(b) by 621 days.

(21) Appl. No.: 17/163,187

(22) Filed: Jan. 29, 2021

(65) Prior Publication Data

US 2021/0353403 A1 Nov. 18, 2021

Related U.S. Application Data

(63) Continuation of application No. 16/300,030, filed as application No. PCT/US2017/032490 on May 12, 2017, now abandoned.
(Continued)

(51) Int. Cl.
*A61F 2/06* (2013.01)
*A61F 2/07* (2013.01)

(52) U.S. Cl.
CPC .......... *A61F 2/06* (2013.01); *A61F 2/07* (2013.01); *A61F 2002/067* (2013.01);
(Continued)

(58) Field of Classification Search
None
See application file for complete search history.

(56) References Cited

U.S. PATENT DOCUMENTS 8,814,928 B2 8/2014 Robin
8,821,564 B2 9/2014 Schreck et al.
(Continued)

FOREIGN PATENT DOCUMENTS

JP 2009-521287 A 6/2009
WO WO-91/07927 A1 6/1991
WO WO-2015/183489 A1 12/2015

OTHER PUBLICATIONS

Chinese Office Action dated Apr. 29, 2020, from application No. 201780036823.1.
(Continued)

*Primary Examiner* — Leslie A Lopez
(74) *Attorney, Agent, or Firm* — Foley & Lardner LLP (57) ABSTRACT

A system for placement in at least one blood vessel includes a main graft body, one or more inflatable channels, and a filling structure. The one or more inflatable channels are attached to the main graft body. The filling structure is inflatable around at least a portion of the main graft body and at least a portion of at least one of the one or more inflatable channels. Various systems further include a graft extension that is insertable into a lumen formed by the main graft body, where the filling structure is inflatable around at least a portion of the graft extension. A method includes inserting a main graft body into a blood vessel, filling an inflatable channel attached to the main graft body, and filling a filling structure to inflate around at least a portion of the main graft body and at least a portion of the inflatable channel.

20 Claims, 9 Drawing Sheets

Related U.S. Application Data (60) Provisional application No. 62/336,547, filed on May 13, 2016.

(52) U.S. Cl.
CPC ... *A61F 2002/075* (2013.01); *A61F 2002/077* (2013.01); *A61F 2220/0016* (2013.01); *A61F 2230/0034* (2013.01); *A61F 2250/0003* (2013.01)

(56) References Cited

U.S. PATENT DOCUMENTS

| | | | |
|---|---|---|---|
| 2004/0204755 A1* | 10/2004 | Robin | A61F 2/07 623/1.21 |
| 2005/0228484 A1 | 10/2005 | Stephens et al. | |
| 2007/0150041 A1* | 6/2007 | Evans | A61F 2/954 623/1.11 |
| 2007/0162106 A1* | 7/2007 | Evans | A61B 17/12195 623/1.36 |
| 2015/0073523 A1 | 3/2015 | Chobotov | |
| 2015/0088244 A1* | 3/2015 | Chobotov | A61F 2/89 623/1.35 |

OTHER PUBLICATIONS

Chinese Office Action dated Mar. 29, 2021, from application No. 201780036823.1.
Extended European Search Report dated Dec. 6, 2019, from application No. 17796968.0.
Final Office Action dated Jul. 31, 2020, from U.S. Appl. No. 16/300,030.
International Preliminary Report on Patentability dated Nov. 22, 2018, from application No. PCT/US2017/032490.
International Search Report and Written Opinion dated Aug. 1, 2017, from application No. PCT/US2017/032490.
Japanese Office Action dated Mar. 29, 2021, from application No. 2018-559824.
Non-Final Office Action dated Apr. 20, 2020, from U.S. Appl. No. 16/300,030.
Chinese Office Action dated Aug. 23, 2021, from application No. 201780036823.1.

* cited by examiner

SYSTEMS AND METHODS WITH GRAFT BODY, INFLATABLE FILL CHANNEL, AND FILLING STRUCTURE

CROSS-REFERENCE TO RELATED PATENT APPLICATIONS

This application claims priority from U.S. application Ser. No. 16/300,030, filed May 12, 2017, which is a national stage entry under U.S.C. § 371 of International Application No. PCT/US2017/032490, filed May 12, 2017, which in turn claims priority from U.S. Provisional Application No. 62/336,547, filed May 13, 2016, the entire contents of each of which are incorporated by reference herein.

FIELD

Embodiments of the present invention relate generally to endoluminal vascular prostheses and methods of placing such prostheses, and in some applications to endoluminal vascular prostheses for use in the treatment of blood vessels.

BACKGROUND

An abdominal aortic aneurysm is a sac caused by an abnormal dilation of the wall of the aorta, a major blood vessel of the body, as it passes through the abdomen. The aorta is the main trunk, or artery, from which the systemic arterial system proceeds with various blood vessels. It arises from the left ventricle of the heart, passes upward, bends over and passes down through the thorax and through the abdomen to about the level of the fourth lumbar vertebra, where it divides into blood vessels called the common iliac arteries.

Some aneurysms arise in the infrarenal portion of the diseased aorta, for example, below the kidneys. When left untreated, the aneurysm may eventually cause rupture of the sac with ensuing fatal hemorrhaging in a very short time. High mortality associated with such ruptures led initially to transabdominal surgical repair of abdominal aortic aneurysms. Surgery involving the abdominal wall, however, is a major undertaking with associated high risks.

Recently, a significantly minimally invasive clinical approach to aneurysm repair, known as endovascular grafting, has been developed, involving the transluminal placement of a prosthetic arterial graft in the endoluminal position within the lumen of the artery. By this method, the graft is attached to the internal surface of an arterial wall by means of attachment devices such as expandable stents, where there may be one stent above the aneurysm and a second stent below the aneurysm.

In certain conditions, the diseased region of the blood vessels extends across branch vessels. The blood flow into these branch vessels is critical for the perfusion of the peripheral regions of the body and vital organs. Many arteries branch off the aorta. For example, the carotid arteries supply blood into the brain, the renal arteries supply blood into the kidneys, the superior mesenteric artery ("SMA") supplies the pancreas, the hypogastric arteries to the reproductive organs, and the subclavian arteries supply blood to the arms. When the aorta is diseased, the branch vessels may also be affected. Thoracic aortic aneurysms may sometimes involve the subclavian and carotid arteries in addition to the aorta, while abdominal aneurysms may sometimes involve the SMA, renal, and hypogastric arteries in addition to the aorta.

SUMMARY OF THE DISCLOSURE

A system in accordance with an embodiment for placement in at least one blood vessel, such as the aorta, includes a main graft body, one or more inflatable channels, and a filling structure. The one or more inflatable channels are attached to the main graft body. The filling structure is inflatable around at least a portion of the main graft body and at least a portion of at least one of the one or more inflatable channels.

In some embodiments, the system further includes a graft extension that is at least partially insertable into a lumen formed by the main graft body. In some embodiments, the filling structure is inflatable around at least a portion of the graft extension. Also, in some embodiments, the filling structure is attached to the graft extension. In various embodiments, the filling structure is attached to the graft extension at two or more discrete locations along a length of the graft extension. In some embodiments, the filling structure is attached to the graft extension only at one or more locations that are away from a proximal end of the graft extension, and the filling structure is expandable around at least a portion of the proximal end of the graft extension.

In some embodiments, the system further includes a second graft extension that is at least partially insertable into the main graft body. In some embodiments, the filling structure is attached to the second graft extension. In some embodiments, the filling structure is insertable into the blood vessel separate from the main graft body, the graft extension, and the second graft extension. In various embodiments, the filling structure is expandable to fill a space between a wall of the at least one blood vessel and each of the at least a portion of the main graft body, the at least a portion of the at least one of the one or more inflatable channels, and at least a portion of the graft extension.

In some embodiments, the filling structure is attached to the main graft body. Also, in some such embodiments, the filling structure is expandable beyond a distal end of the main graft body. In some embodiments, a particular inflatable channel of the one or more inflatable channels is located between a proximal end of the main graft body and a location of attachment of the filling structure to the main graft body. In some embodiments, a second particular inflatable channel of the one or more inflatable channels is located between a distal end of the main graft body and the location of attachment of the filling structure to the main graft body. In some embodiments, the system further includes a second filling structure inflatable around at least a portion of the filling structure.

A method in accordance with an embodiments includes inserting a main graft body into at least one blood vessel, filling one or more inflatable channels attached to the main graft body, and filling a filling structure to inflate around at least a portion of the main graft body and at least a portion of at least one of the one or more inflatable channels. In some embodiments, the filling structure is attached to the main graft body. In some embodiments, the method further includes inserting at least a portion of a graft extension into a lumen formed by the main graft body, and the filling structure extends around at least a portion of the graft extension. In some embodiments, the filling structure is attached to a graft extension and the method further includes inserting at least a portion of the graft extension into a lumen formed by the main graft body. In some embodiments, the method further includes filling a second filling structure to inflate around at least a portion of the filling structure.

A system in accordance with an embodiment includes a main graft body and a filling structure. In various embodiments, at least one circumferential inflatable channel is disposed towards a proximal portion of the main graft body near a proximal open end of the main graft body, and a plurality of circumferential inflatable channels are disposed towards a distal portion of the main graft body near a distal open end of the main graft body. In various embodiments, the filling structure defines an internal volume that is fillable with a filling medium and is expandable around at least a portion of the plurality of circumferential inflatable channels disposed towards the distal portion of the main graft body.

DETAILED DESCRIPTION

The following detailed description is now directed to certain embodiments of the disclosure. In this description, reference is made to the drawings wherein like parts are designated with like numerals throughout the description and the drawings.

Certain embodiments described herein are directed to systems, methods, and apparatuses to treat lesions, aneurysms, or other defects in blood vessels such as the aorta, including, but not limited to, the thoracic, ascending, and abdominal aorta. However, the systems, methods, and apparatuses may have application to other areas of the body, or to other fields, and such additional applications are intended to form a part of this disclosure. For example, it will be appreciated that the systems, methods, and apparatuses may have application to the treatment of blood vessels in animals. Various embodiments and/or aspects of the endoluminal prosthesis systems, methods, and apparatuses described herein can be applied to other parts of the body or may have other applications apart from the treatment of the thoracic, ascending, and abdominal aorta. And, while specific embodiments may be described herein with regard to particular portions of the aorta, it is to be understood that the embodiments described can be adapted for use in other portions of the aorta or other portions of the body and are not limited to the aortic portions described.

With regard to graft embodiments discussed herein, such as the endoluminal prosthesis systems, and components thereof, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

Figure 1:
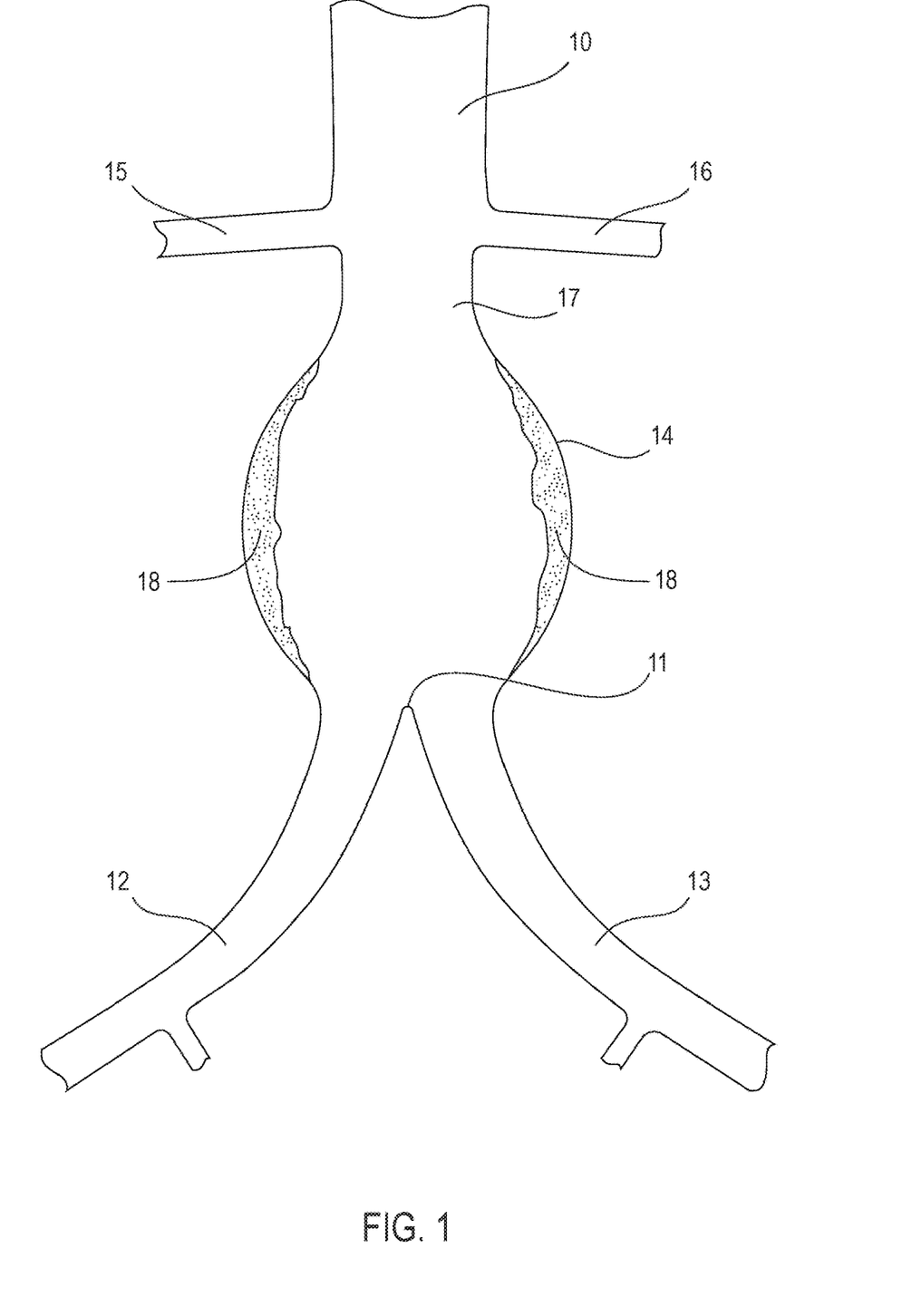
FIG. 1 is an illustration of a cross section of an example patient anatomy with an infrarenal aortic aneurysm.

FIG. 1 is an illustration of a cross section of an example patient anatomy with an infrarenal aortic aneurysm. In FIG. 1, an aorta 10 branches at an aortic bifurcation 11 into two iliac arteries 12 and 13. An aneurysm sac 14 denotes a bulged section of the aorta 10. As the name implies, the infrarenal aortic aneurysm is located below renal arteries 15 and 16. A segment of the aorta 10 between the renal arteries 15 and 16 and the aneurysm sac 14 is referred to as a proximal neck 17. Often mural thrombus 18 forms on an inside wall of the aneurysm sac 14.

Figure 2:
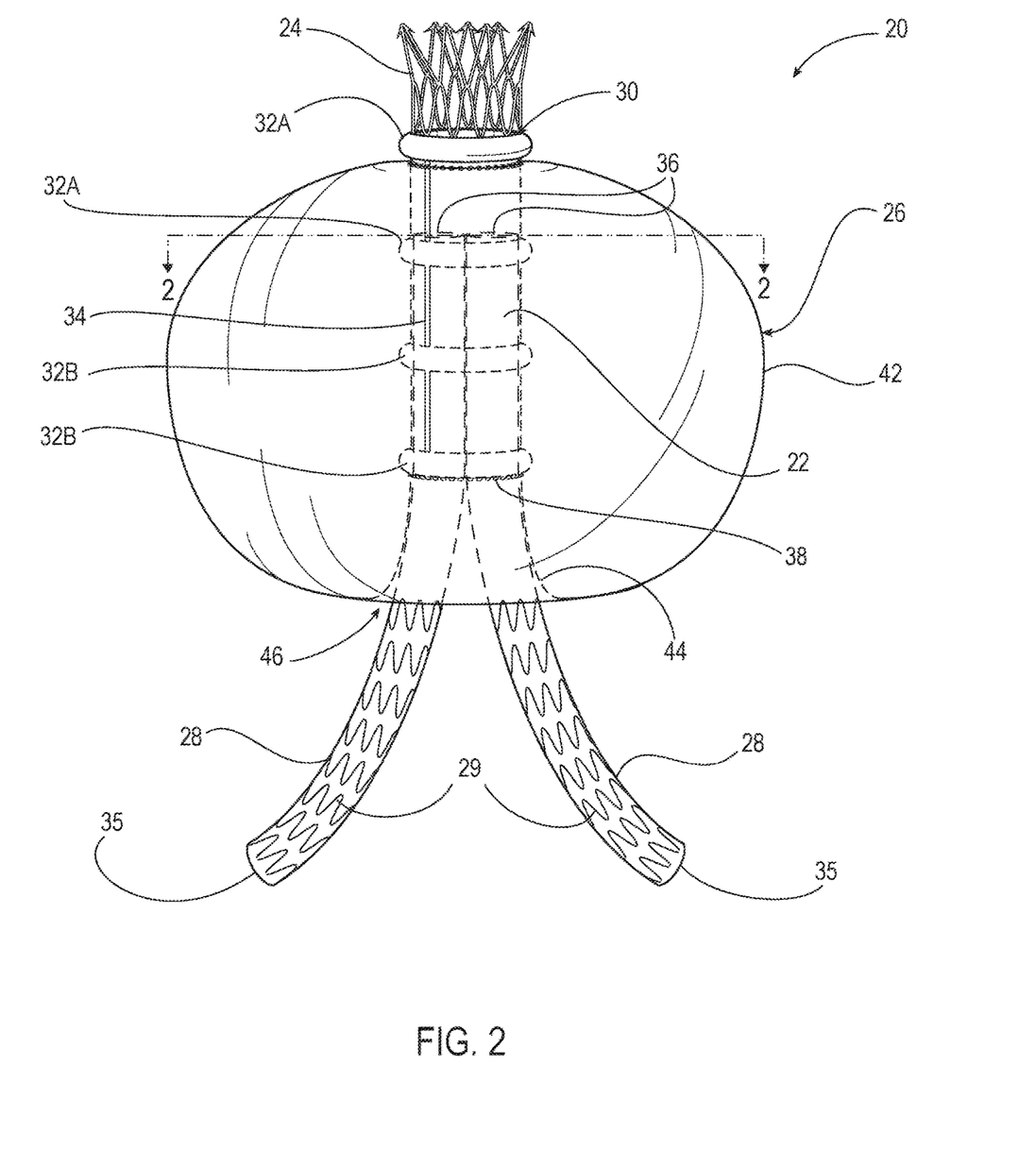
FIG. 2 is a front elevation view of an endoluminal prosthesis system according to an exemplary embodiment.
Figure 3:
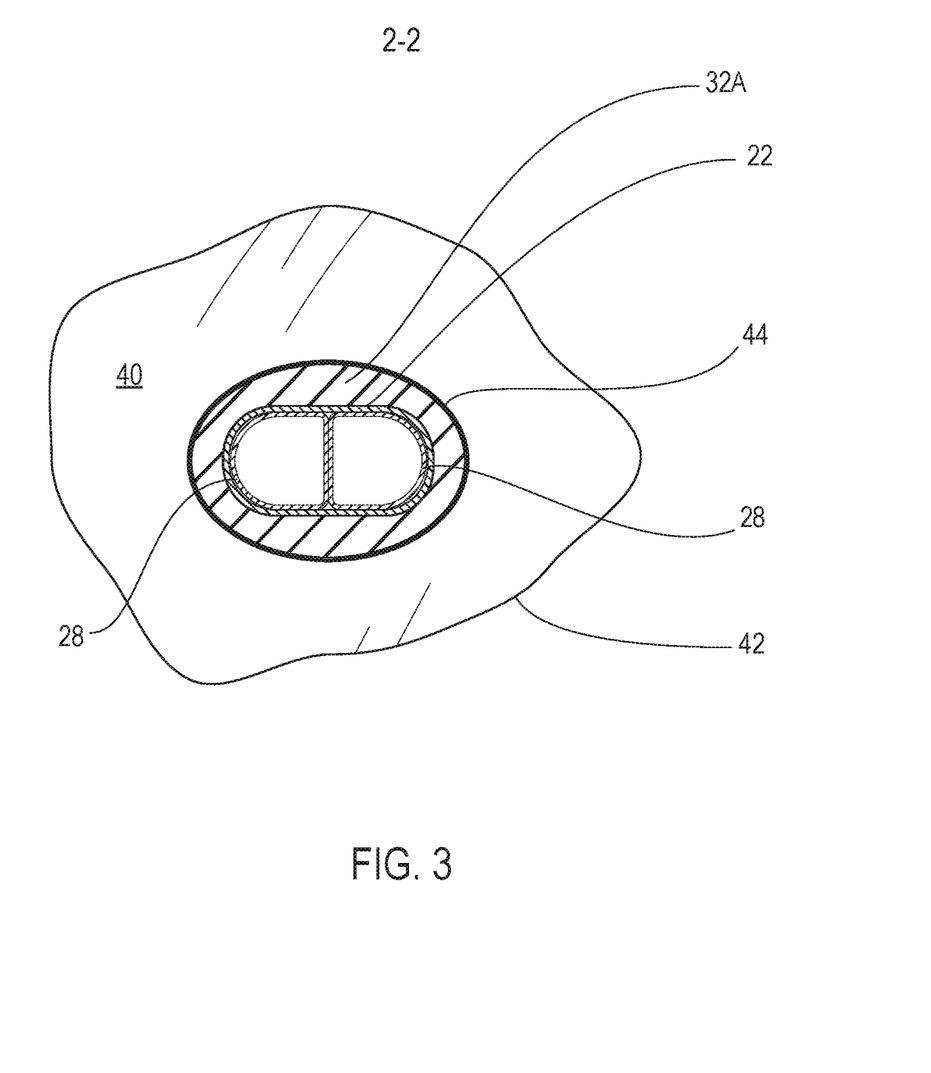
FIG. 3 is a cross section view of the endoluminal prosthesis system of FIG. 2 along the line 2-2.
Figure 4:
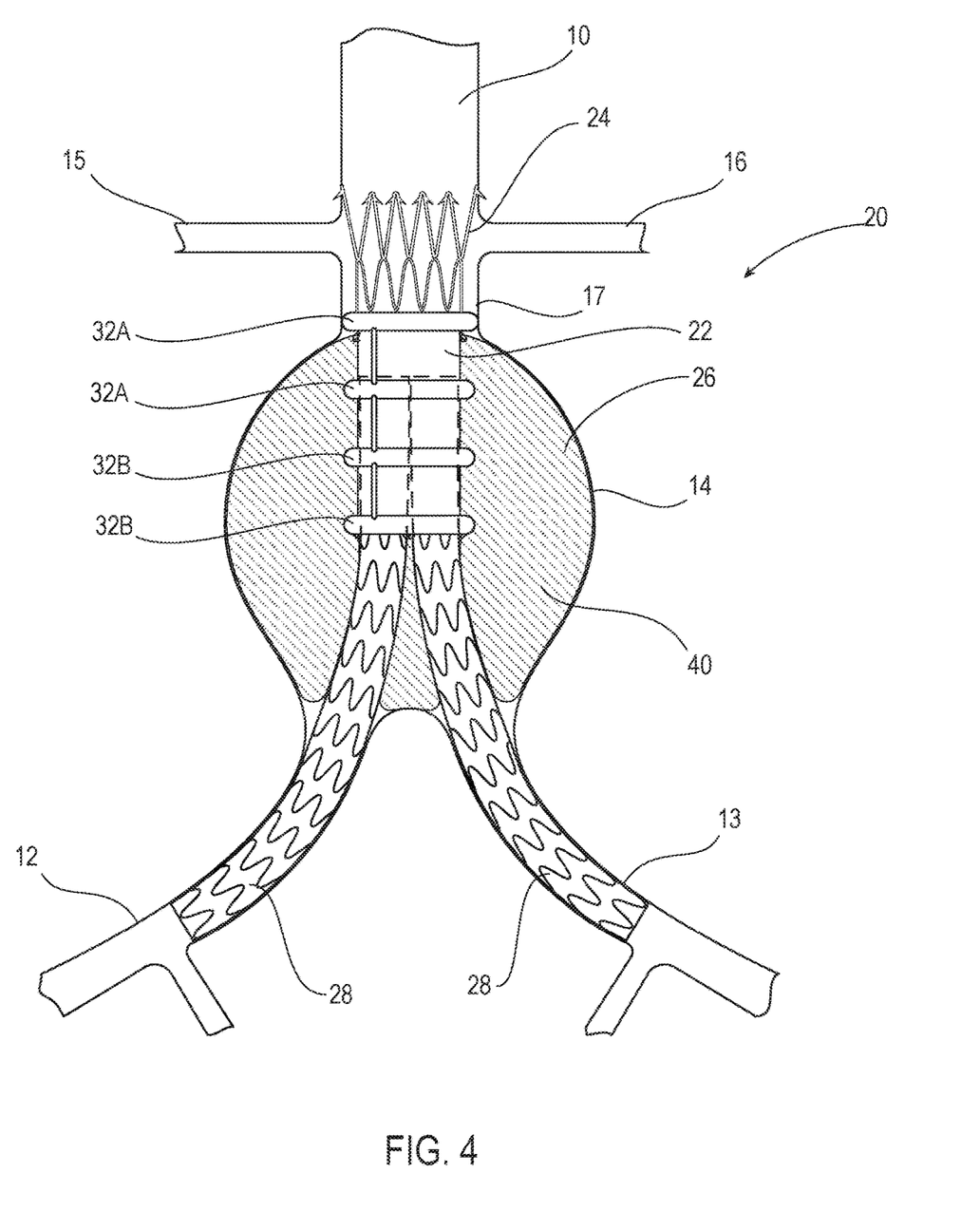
FIG. 4 is an illustration of the endoluminal prosthesis system of FIG. 2 deployed to repair an aneurysm.

FIG. 2 is a front elevation view of an endoluminal prosthesis system 20 according to an exemplary embodiment. FIG. 3 is a cross section view taken through line 2-2 of FIG. 2. FIG. 4 shows the endoluminal prosthesis system 20 of FIG. 2 deployed to repair an aneurysm in an aorta 10. With reference to FIGS. 2, 3, and 4, the endoluminal prosthesis system 20 includes a main graft body 22, inflatable channels 32A and 32B, a filling structure 26, graft extensions 28, and a proximal anchor member 24. In various embodiments the filling structure 26 is a double-walled filling structure positionable in the area of an aneurysm. In various embodiments, the graft extensions 28 are at least partially insertable into a lumen 30 formed by the main graft body 22 so as to extend from the distal end of the main graft body 22.

The main graft body 22 defines the central lumen 30. The main graft body 22 provides a synthetic vessel wall that channels the flow of blood through a diseased portion of at least one blood vessel (e.g., the aorta). In some embodiments, the main graft body 22 has a generally cylindrical, tubular shape. The endoluminal prosthesis system 20 can be formed from any suitable material, such as, but not limited to, Polytetrafluoroethylene (PTFE), expanded PTFE (ePTFE), and/or paralyne. In various embodiments, the main graft body 22 is formed from one or more layers of graft material, such as PTFE or ePTFE. For some embodiments, the main graft body 22 has an axial length of about 5 cm to about 10 cm and, in some embodiments, about 6 cm to about 8 cm, in order to span an aneurysm of a patient's aorta.

A network of inflatable elements, such as the inflatable channels 32A and 32B, is attached to or disposed on the main graft body 22, such as by an adhesive, sutures, or by being integral with the main graft body 22. In some embodiments, the endoluminal prosthesis system 20 include at least one proximal circumferential inflatable channel (shown as the inflatable channels 32A) and at least one distal circumferential inflatable channel (shown as the inflatable channels 32B). In some embodiments, each of the inflatable channels 32A and 32B extends around an entire circumference of the main graft body 22. In some embodiments, one or more of the inflatable channels 32A and 32B only extends partially around the circumference of the main graft body 22. In various embodiments, the inflatable channels 32A and 32B are in communication with each other, such as in fluid communication with each other, via a longitudinal inflatable fill channel 34. In various embodiments, the longitudinal inflatable fill channel 34 is a tubular structure that is designed to allow fluid communication among the interiors of the inflatable channels 32A and 32B.

In various embodiments, the inflatable channels 32A and 32B are inflated under pressure with an inflation material or filling material or medium through the longitudinal inflatable fill channel 34 that forms a lumen in fluid communication with the network of inflatable channels 32A and 32B. In some embodiments, the inflation material is retained within the network of inflatable channels 32A and 32B by a one way-valve disposed within the lumen of the longitudinal inflatable fill channel 34. In some embodiments, the network of inflatable channels 32A and 32B are filled with an inflation material that is a hardenable material that is configured to harden, cure, or otherwise increase in viscosity or become more rigid after being injected into the inflatable channels 32A and 32B. As the inflation material passes through the longitudinal inflatable fill channel 34, each of the inflatable channels 32A and 32B are filled with inflation material. In addition, in various embodiments the longitudinal inflatable fill channel 34 is also filled with the inflation material to result in a rigid and strong endoluminal prosthesis system 20.

Hardenable filling mediums or inflation materials such as gels, liquids, or other flowable materials that are curable to a more solid or substantially hardened state may be used to provide mechanical support to the main graft body 22 by virtue of the mechanical properties of the hardened material disposed within the inflatable channels 32A and 32B. In various embodiments, the network of inflatable channels 32A and 32B provides structural support to the main graft body 22 when in an inflated state due to the stiffness of the inflatable channels 32A and 32B. In some embodiments, the network of inflatable channels 32A and 32B provides structural support to the main graft body 22 when in an inflated state due to the stiffness of the inflatable channels 32A and 32B caused by an increased interior pressure within the inflatable channels 32A and 32B even if a non-hardenable inflation material, such as saline or the like, is used so long as an increased interior pressure can be maintained. Such an increase in stiffness or rigidity may be useful for a variety of purposes.

For example, during deployment, inflation of the network of inflatable channels 32A and 32B may urge the main graft body 22 to conform to a generally cylindrical configuration having an open flow lumen which may be useful when attempting to locate and navigate the flow lumen with a delivery catheter, guidewire, or the like. Such location and navigation of the flow lumen may also be facilitated by the use of radiopaque inflation materials that provide enhanced visualization under fluoroscopic imaging.

In various embodiments, the inflatable channels 32A and 32B are configured to accept a hardenable fill material to provide structural rigidity to the main graft body 22 when the inflatable channels 32A and 32B are in an inflated state and the fill material has been cured or hardened. Radiopaque fill material may be used to facilitate monitoring of the fill process of the inflatable channels 32A and 32B and subsequent engagement of the graft extensions 28. In some embodiments, at least one of the inflatable channels 32A, such as the most proximal of the inflatable channels 32A is an inflatable cuff disposed on a proximal portion of the main graft body 22 and is configured to be expandable to seal against an inside surface of a patient's blood vessel, such as to seal against the proximal neck 17 portion of the aorta 10 above the aneurysm sac 14. In various embodiments, there may be more than one inflatable fill channel 34 with each of them connected to a different group of one or more of the inflatable channels 32A and 32B.

In various embodiments, the graft extensions 28 are formed from an inner layer or layers and outer layer or layers of flexible graft material, such as PTFE or ePTFE. The inner and outer layers of graft material may be formed from tubular extrusions, laminated wraps of multiple layers of graft material or materials, and/or the like. The inner or outer layers of graft material may be permeable, semi-permeable or substantially non-permeable for some embodiments. For some embodiments, the nominal length of the graft extensions 28 may be permeable with one or more longitudinal sections, such as a middle longitudinal section, being semi-permeable or non-permeable. Some embodiments of each of the graft extensions 28 may have an overall tapered or flared configuration with a nominal inner lumen that tapers or flares when the graft extension 28 is in a relaxed expanded state. For embodiments that include laminated wraps of material, the wraps may be carried out circumferentially, helically, or in any other suitable configuration. In various embodiments, the graft extensions 28 are stent-graft devices with a stent 29 attached to or integrated within graft material. For example, in some embodiments, each of the graft extensions 28 includes a radially expandable stent 29 interposed between an outer layer and inner layer of graft material.

For some embodiments, the stent 29 of each of the graft extensions 28 is an interposed self-expanding stent disposed between at least one outer layer and at least one inner layer of supple layers of graft material. The interposed stent 29 disposed between the outer layer and inner layer of graft material may be formed from an elongate resilient element helically wound with a plurality of longitudinally spaced turns into an open tubular configuration. In some embodiments, the stent 29 of each of the graft extensions 28 has a winding, undulating configuration from the proximal end to the distal end of the stent 29. For some embodiments, the stent 29 of each of the graft extensions 28 is formed from a super-elastic alloy such as super-elastic NiTi alloy known as Nitinol. In addition, the graft material of each graft extension 28 may further include at least one axial zone of low permeability for some embodiments.

In various embodiments, each of the graft extensions 28 is deployed through a corresponding iliac artery 12, 13 via a corresponding catheter. The graft extensions 28 may be deployed in separate stages or substantially and/or approximately in a simultaneous manner with each other. A proximal end 36 of each of the graft extensions 28 is insertable into the central lumen 30 of the main graft body 22. In various embodiments, upon expansion of the stents 29 of the graft extensions 28 and upon inflation of the inflatable channels 32A and 32B, the graft extensions 28 conform to a shape of an inner surface of the main graft body 22 and to each other in vivo to eliminate gutters between components. In various embodiments, distal ends 35 of the graft extensions 28 are deployable within respective iliac arteries 12, 13, such that the graft extensions 28 extend out of a distal end portion 38 of the main graft body 22 into the respective iliac arteries 12, 13. Some embodiments may also employ radiopaque inflation material to facilitate monitoring of the fill process and subsequent engagement of the graft extensions 28. In various embodiments, at least one of the inflatable channels 32B is utilized for visualization of a distal opening of the main graft body 22 and conformance to the inserted graft extensions 28 to aid in minimizing gutters between components.

In various embodiments, the graft extensions 28 are disposed side by side into the main graft body 22, with their proximal ends 36 extending near or within an area surrounded by one or more of the proximal circumferential inflatable channels 32A. Further improvement of ring apposition may be achieved in various embodiments by deploying the graft extensions 28 such that the proximal end 36 of each graft extension 28 is disposed inside an area surrounded by at least one of the inflatable channels 32A. In some embodiments, proximal ballooning is accomplished with kissing balloons, and kissing balloon expandable stents are utilized for the graft extensions 28.

In various embodiments, the filling structure 26 surrounds the main graft body 22 and, when inflated, occupies the annular space in the aneurysm sac 14 between the main graft body 22 and the walls of the aorta 10 or other blood vessel. The filling structure 26 defines an internal volume 40 defined between an outer wall 42 of the filling structure 26 and an inner wall 44 of the filling structure 26. In various embodiments, the inner wall 44 defines an inner lumen 46, and the inner lumen 46 is configured to receive the main graft body 22 and the graft extensions 28. In various embodiments, a geometry of the filling structure 26 is chosen or fabricated to match a particular patient geometry being treated. Upon inflation with a filling material or medium delivered into the internal volume 40 of the filling structure 26, the outer wall 42 expands radially outward.

In various embodiments, the filling structure 26 includes at least one valve to permit the introduction of filling material or medium into the internal volume 40 of the filling structure 26. In some embodiments, the valve includes a simple flap valve. In some embodiments, the valve comprises other more complex ball valves or other one-way valve structures. In some embodiments, the valve comprises a two-way valve structure to permit both filling and selective emptying of the internal volume 40. In some embodiments, a filling tube includes a needle or other filling structure to pass through the valve to permit both filling and removal of filling medium.

In various embodiments of the endoluminal prosthesis system 20, the filling structure 26 is integrally formed with the main graft body 22. For example, in some embodiments, the main graft body 22 forms at least a portion of the inner wall 44 of the filling structure 26. In some embodiments, the inner wall 44 of the filling structure 26 is coupled to or attached to the main graft body 22 with an adhesive or other suitable attachment mechanism such as sutures or the like. In some embodiments, the main graft body 22 also has attached to it the inflatable channel 32A and 32B that are not in fluid communication with the internal volume 40 of the filling structure 26. In various embodiments, the inflatable channels 32A and 32B and the filling structure 26 are filled separately through separate valves. In various embodiments, the filling structure 26 forms an annular, donut-like structure around the main graft body 22, one or more of the inflatable channels 32A and 32B, and at least a portion of each of the graft extensions 28. In various embodiments, the filling structure 26 is a bag, such as an endobag or the like. In various embodiments, the filling structure 26 is fillable with a hardenable filling material such as Polyethylene glycol (PEG) or another polymer that may be polymerized in situ.

In various embodiments, the graft extensions 28 are deployed side-by-side within the inner lumen 46 of the filling structure 26 prior to inflation of the filling structure 26. This allows the filling structure 26 to conform to the edges of the parallel graft extensions 28. In various embodiments, a delivery system includes a fill line with a fill lumen for the filling structure 26 that is slidably integrated such that a main delivery catheter can be withdrawn while the fill lumen stays behind, still connected to the filling structure 26 and ready for filling (e.g., by attaching a slip connected luer fitting over its end).

In various embodiments, the filling structure 26 surrounds the main graft body 22. The filling structure 26 defines the internal volume 40. In various embodiments, the internal volume 40 is configured to accept a hardenable inflation or fill material. Radiopaque inflation material and/or radiopaque markers may be used to facilitate monitoring of the fill process. In some embodiments, the filling structure 26 is coupled to the main graft body 22, the proximal anchor member 24, and/or one or more of the graft extensions 28 to maintain a desired alignment. In various embodiments, the filling structure 26 is coupled to the main graft body 22 near a proximal end of the main graft body 22 with sutures, with an adhesive, or with another suitable attachment mechanism, and is coupled to the main graft body 22 near a distal end of the main graft body 22 with sutures, with an adhesive, or with another suitable attachment mechanism.

In various embodiments, the proximal anchor member 24 is positionable across the renal arteries 15, 16 to maintain blood there through. In various embodiments, the proximal anchor member 24 serves to anchor the endoluminal prosthesis system 20 within the aorta 10. In various embodiments, one or more of the inflatable channels 32A is positioned above the aneurysm sac 14 in the aorta 10 and above the filling structure 26 and upon inflation seals against the proximal neck 17 portion of the aorta 10 above the aneurysm sac 14. In various embodiments, after the main graft body 22 and the proximal anchor member 24 are deployed, the graft extensions 28 are deployed.

In various embodiments, the proximal anchor member 24 is disposed at a proximal end of the main graft body 22 and is secured to the main graft body 22. In various embodiments, the proximal anchor member 24 has an expanding (e.g., self-expanding, balloon expanded, etc.) proximal stent portion secured to an expanding distal stent portion with struts. Some embodiments of the struts may have a cross sectional area that is substantially the same as or greater than a cross sectional area of proximal stent portions or distal stent portions adjacent the strut. Such a configuration may be useful in avoiding points of concentrated stress in the proximal anchor member or struts which couple components thereof. For some embodiments, the proximal anchor member 24 further includes a plurality of barbs having sharp tissue engaging tips that are configured to extend in a radial outward direction in a deployed expanded state to secure the proximal anchor member 24 to a wall of a blood vessel, such as a wall of the aorta 10. For some embodiments, the proximal anchor member 24 includes a four crown proximal stent portion and an eight crown distal stent portion that are made from a super-elastic alloy such as super-elastic nitinol (NiTi) alloy.

The endoluminal prosthesis system 20 is positionable in at least one blood vessel, such as the aorta 10. In various embodiments, the inflatable channels 32A and 32B are attached to the main graft body 22. In various embodiments, the filling structure 26 is inflatable around at least a portion of the main graft body 22 and at least a portion of at least one of the inflatable channels 32A, 32B. In various embodiments, the filling structure 26 is inflated by filling the filling structure 26 with a hardenable fill material or medium. In some embodiments, the endoluminal prosthesis system includes the graft extensions 28 that are at least partially insertable into the central lumen 30 formed by the main graft body 22. In some embodiments, the filling structure 26 is inflatable around at least a portion of each of the graft extensions 28.

In some embodiments, the filling structure 26 is attached to the main graft body 22. Also, in some embodiments, the filling structure 26 is expandable beyond a distal end of the main graft body 22. In some embodiments, a particular inflatable channel of the inflatable channels 32A is located between a proximal end of the main graft body 22 and a location of attachment of the filling structure 26 to the main graft body 22. For example, the filling structure 26 is attached to the main graft body 22 below a top one of the inflatable channels 32A. In some embodiments, a particular inflatable channel of the inflatable channels 32B is located between a distal end of the main graft body 22 and a top location of attachment of the filling structure 26 to the main graft body 22. In some embodiments, the filling structure 26 is insertable into a blood vessel separate from the main graft body 22 and the graft extensions 28. In various embodiments, the filling structure 26 is expandable to fill a space between a wall of the blood vessel, such as the wall of the aneurysm sac 14 in the aorta 10, and each of at least a portion of the main graft body 22, at least a portion of one or more of the inflatable channels 32A, 32B, and at least a portion of the graft extensions 28.

Figure 5:
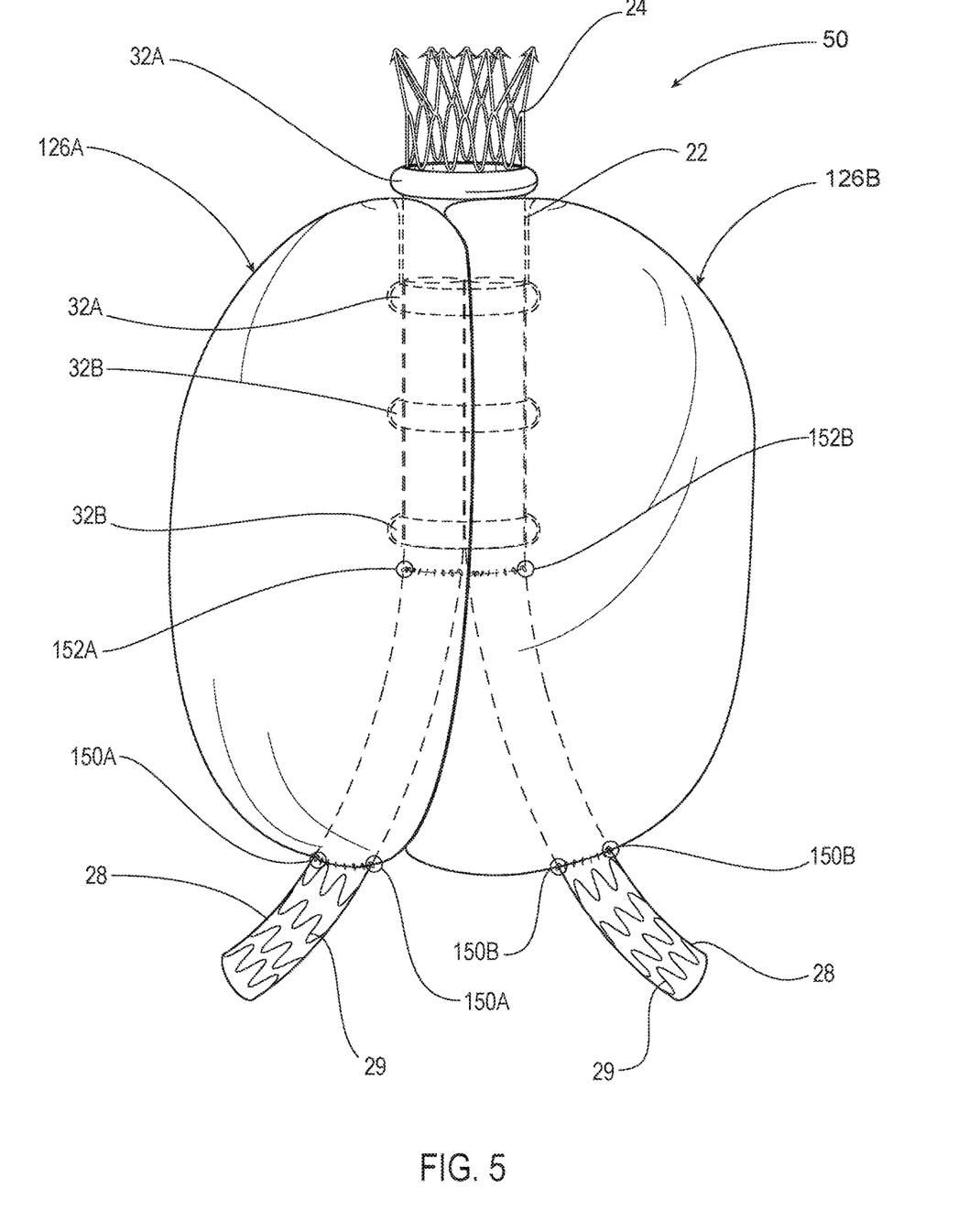
FIG. 5 is a front elevation view of an endoluminal prosthesis system according to another exemplary embodiment.
Figure 6:
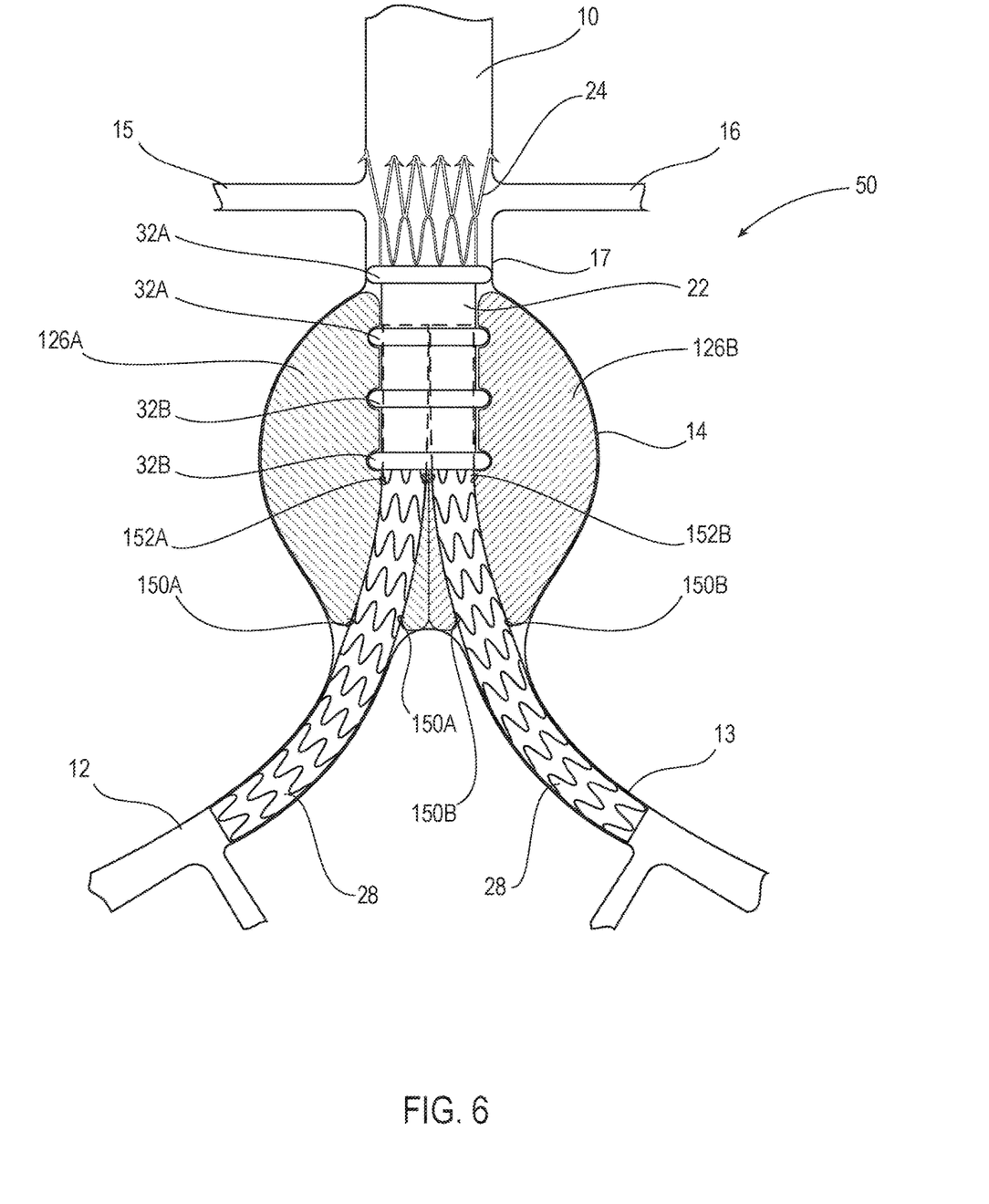
FIG. 6 is an illustration of the endoluminal prosthesis system of FIG. 5 deployed to repair an aneurysm.

Referring now to FIG. 5, a front elevation view of an endoluminal prosthesis system 50 is shown according to another exemplary embodiment. FIG. 6 is an illustration of the endoloumninal prosthesis system 50 of FIG. 5 deployed to repair an aneurysm in the aorta 10. With reference to FIGS. 5 and 6, the endoluminal prosthesis system 50 includes the main graft body 22, the inflatable channels 32A and 32B, the graft extensions 28, and the proximal anchor member 24. The endoluminal prosthesis system 50 further includes multiple filling structures 126A and 126B, with each of the filling structures 126A and 126B coupled to a respective one of the graft extensions 28. According to an exemplary embodiment, the filling structures 126A and 126B are each coupled to a respective one of the graft extensions 28 with one or more sutures (e.g., sutured to the stent 29), with an adhesive, or with another suitable attachment mechanism.

In some embodiments, the filling structure 126A is coupled to a respective one of the graft extensions 28 at at least a distal attachment point 150A and a proximal attachment point 152A, with the proximal attachment point 152A being just distal to a distal end of the main graft body 22. In some embodiments, the filling structure 126B is coupled to a respective one of the graft extensions 28 at at least a distal attachment point 150B and a proximal attachment point 152B, with the proximal attachment point 152B being just distal to a distal end of the main graft body 22. In some embodiments, the filling structures 126A and 126B are formed to have a proximal biased shape. In some embodiments, the filling structures 126A and 126B are filled separately, through separate openings and through separate filling lumens. In some embodiments, the filling structures 126A and 126B are in fluid communication with each other and are filled with a same filling lumen.

The endoluminal prosthesis system 50 is positionable in at least one blood vessel, such as the aorta 10. In various embodiments, the one or more inflatable channels 32A and 32B are attached to the main graft body 22. The filling structure 126A is inflatable around at least a portion of the main graft body 22 and at least a portion of at least one of the inflatable channels 32A and 32B, and around at least a portion of a respective one of the graft extensions 28. The filling structure 126B is inflatable around at least a portion of the main graft body 22 and at least a portion of at least one of the inflatable channels 32A and 32B, and around at least a portion of a respective one of the graft extensions 28.

The graft extensions 28 are at least partially insertable into a lumen formed by the main graft body 22. In various embodiments, the filling structure 126A is attached to a respective one of the graft extensions 28 at two or more discrete locations along a length of the graft extension, such as at the distal attachment point 150A and the proximal attachment point 152A. In some embodiments, the filling structure 126A is attached to the respective graft extension 28 only at one or more locations that are away from a proximal end of the graft extension 28, and the filling structure 126A is expandable around at least a portion of the proximal end of the respective graft extension 28. In some embodiments, the filling structure 126A is attached to both of the graft extensions 28.

In various embodiments, the filling structure 126A is expandable to fill a space between a wall of the aneurysm sac 14 and each of at least a portion of the main graft body 22, at least a portion of at least one of the inflatable channels 32B, and at least a portion of the respective graft extension 28 to which the filling structure 126A is attached. In various embodiments, the filling structure 126B is expandable to fill a space between a wall of the aneurysm sac 14 and each of at least a portion of the main graft body 22, at least a portion of at least one of the inflatable channels 32B, and at least a portion of the respective graft extension 28 to which the filling structure 126B is attached.

In various embodiments, the proximal anchor member 24 is positionable across the renal arteries 15, 16 to maintain blood there through and serves to anchor the endoluminal prosthesis system 50 within the aorta 10. In various embodiments, distal ends of the graft extensions 28 are deployable within respective iliac arteries 12, 13, such that the graft extensions 28 extend out of a distal end portion of the main graft body 22 into the respective iliac arteries 12, 13. In various embodiments, one or more of the inflatable channels 32A is positioned above the aneurysm sac 14 in the aorta 10 and above the filling structures 126A and 126B, and upon inflation seals against the proximal neck 17 portion of the aorta 10 above the aneurysm sac 14.

Figure 7:
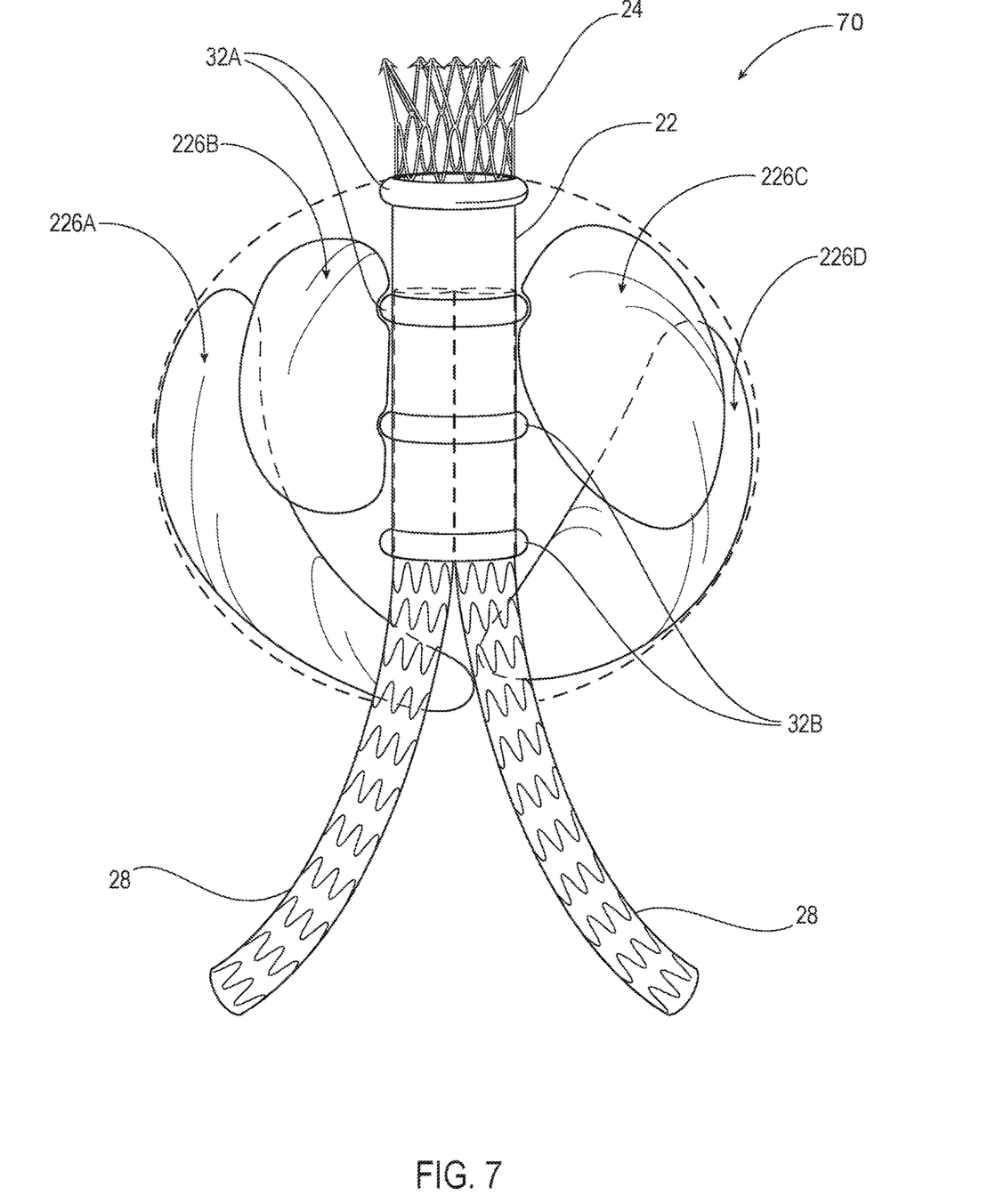
FIG. 7 is a front elevation view of an endoluminal prosthesis system according to another exemplary embodiment.
Figure 8:
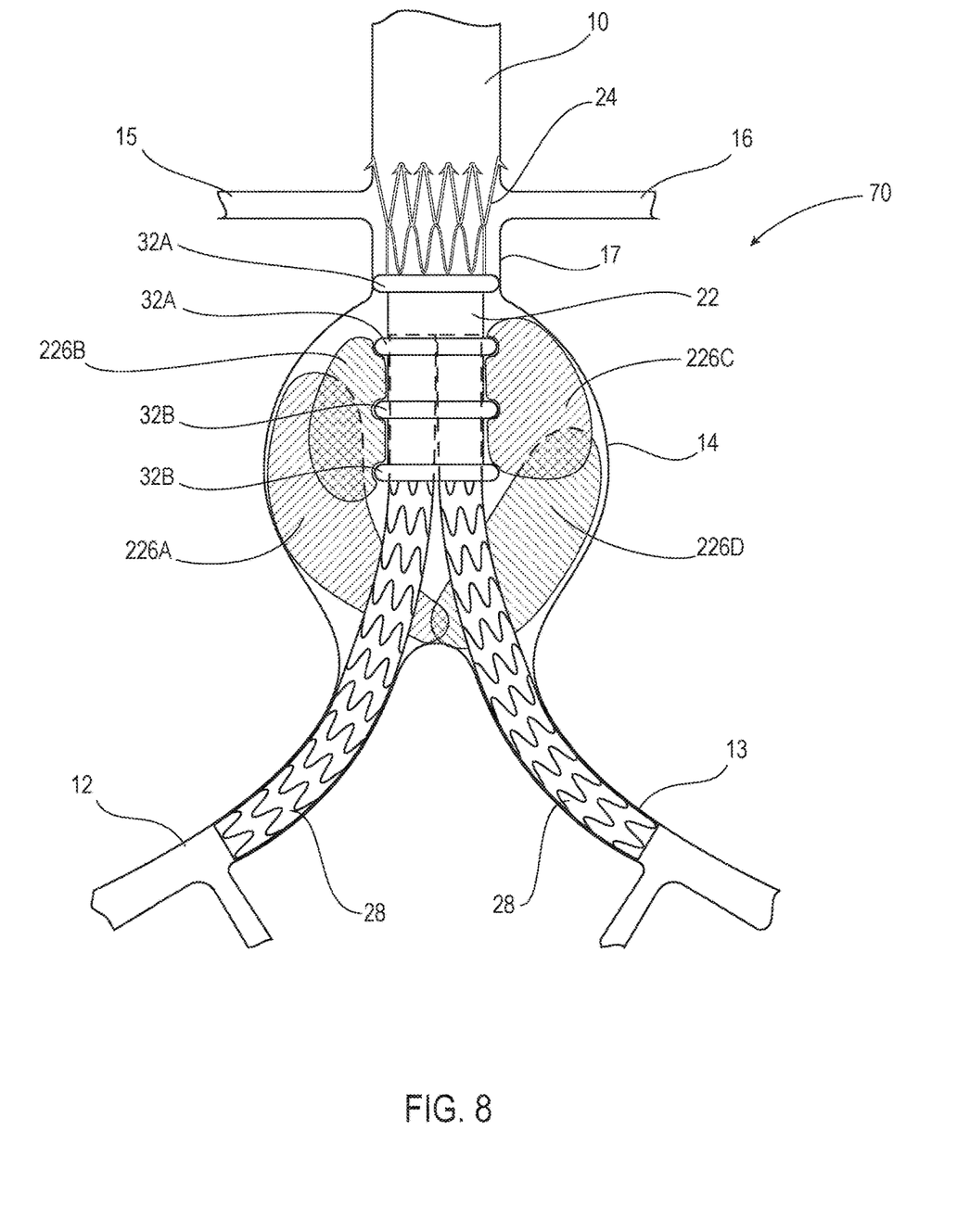
FIG. 8 is an illustration of the endoluminal prosthesis system of FIG. 7 deployed to repair an aneurysm.

Referring now to FIG. 7, a front elevation view of an endoluminal prosthesis system 70 is shown according to another exemplary embodiment. FIG. 8 is an illustration of the endoloumninal prosthesis system 70 of FIG. 7 deployed to repair an aneurysm in the aorta 10. With reference to FIGS. 7 and 8, the endoluminal prosthesis system 70 includes the main graft body 22, the inflatable channels 32A and 32B, the graft extensions 28, and the proximal anchor member 24. The endoluminal prosthesis system 50 further includes multiple filling structures 226A, 226B, 226C, and 226D. In various embodiments, the filling structures 226A, 226B, 226C, and 226D are deliverable to the aneurysm separately from both the main graft body 22 and the graft extensions 28. In some embodiments, the filling structures 226A, 226B, 226C, and 226D are delivered to the site of the aneurysm prior to the delivery of any of the graft extensions 28. In some embodiments, the filling structures 226A, 226B, 226C, and 226D are delivered to the site of the aneurysm subsequent to delivery of at least one of the graft extensions 28.

The endoluminal prosthesis system 70 is positionable in at least one blood vessel, such as the aorta 10. In various embodiments, the one or more inflatable channels 32A and 32B are attached to the main graft body 22. The filling structure 226B is inflatable around at least a portion of the main graft body 22 and at least a portion of at least one of the inflatable channels 32A and 32B. The filling structure 226A is inflatable around at least a portion of the filling structure 226B and is expandable to contact a wall of the aneurysm sac 14 in the aorta 10. The filling structure 226C is inflatable around at least a portion of the main graft body 22 and at least a portion of at least one of the inflatable channels 32A and 32B. The filling structure 226D is inflatable around at least a portion of the filling structure 226C and is expandable to contact a wall of the aneurysm sac 14 in the aorta 10. The filling structures 226A and 226D are also each inflatable around at least a portion of a corresponding one of the graft extensions 28. The graft extensions 28 are at least partially insertable into a lumen formed by the main graft body 22.

In various embodiments, the proximal anchor member 24 is positionable across the renal arteries 15, 16 to maintain blood there through and serves to anchor the endoluminal prosthesis system 70 within the aorta 10. In various embodiments, distal ends of the graft extensions 28 are deployable within respective iliac arteries 12, 13, such that the graft extensions 28 extend out of a distal end portion of the main graft body 22 into the respective iliac arteries 12, 13. In various embodiments, one or more of the inflatable channels 32A is positioned above the aneurysm sac 14 in the aorta 10 and above the filling structures 226A, 226B, 226C, and 226D, and upon inflation seals against the proximal neck 17 portion of the aorta 10 above the aneurysm sac 14.

An endoluminal prosthesis in accordance with various embodiments includes a main endoluminal prosthesis having a network of inflatable channels and a main graft body, one or more graft extensions, a proximal anchor member, and one or more double-walled filling structures positionable in the area of an aneurysm. The endoluminal prosthesis in accordance with various embodiments is described herein as being positioned in the abdominal aorta with the graft extensions extending into the iliac branches. In some configurations, the endoluminal prosthesis may be placed suprarenal, and may include additional graft extensions extending from the main graft body through one or more vessels branching from the aorta (e.g., left renal artery, right renal artery, second lumbar, testicular, inferior mesenteric, middle sacral, etc.). Thus, in some embodiments, the endoluminal prosthesis can include any number of elements that are required for the specific application, including, but not limited to, elements for one, two, three, or more branch arteries. Because the elements disposed in the branch arteries can be configured to conform to a wide range of vessels and a wide range of positions, the elements can be of any suitable size, shape, or configuration, and can be attached to the main graft body in any of a wide variety of locations.

The endoluminal prosthesis may be bifurcated. The endoluminal prosthesis may be formed from a supple graft material, such as expanded polytetrafluoroethylene (ePTFE), having a main fluid flow lumen therein. The endoluminal prosthesis may include porous polytetrafluoroethylene (PTFE) which has no discernable node and fibril structure. A bifurcated endoluminal prosthesis may also include an ipsilateral leg with an ipsilateral fluid flow lumen in communication with the main fluid flow lumen, a contralateral leg with a contralateral fluid flow lumen in communication with the main fluid flow lumen, and a network of inflatable channels disposed on the main graft body.

The inflatable channels of the network of inflatable channels may be disposed on any portion of the endoluminal prosthesis including the main body portion, as well as the ipsilateral and contralateral legs. The network of inflatable channels may be configured to accept a hardenable fill material to provide structural rigidity to the main graft body when the network of inflatable channels are in an inflated state and the inflation material has been cured or hardened. Radiopaque inflation material may be used to facilitate monitoring of the fill process and subsequent engagement of graft extensions. The network of inflatable channels may also include at least one inflatable cuff disposed on a proximal portion of the main graft body which is configured to seal against an inside surface of a patient's vessel, such as the aorta. The network of inflatable channels may include at least one longitudinal fill channel in communication with channels at the proximal and distal ends of the device. Further, the network of inflatable channels may include a longitudinal channel in communication with circumferential channels at one end of the device.

The graft extensions may be disposed at the distal end of the main graft body. For a bifurcated endoluminal prosthesis, at least one ipsilateral graft extension having a fluid flow lumen disposed therein may be deployed with the fluid flow lumen of the graft extension sealed to and in fluid communication with the fluid flow lumen of the ipsilateral leg of the main graft body. In addition, at least one contralateral graft extension having a fluid flow lumen disposed therein may be deployed with the fluid flow lumen of the graft extension sealed to and in fluid communication with the fluid flow lumen of the contralateral leg of the main graft body.

Some arrangements disclosed herein are directed to systems and methods of deploying an endoluminal prosthesis system, such as, without limitation, the endoluminal prostheses systems described above, including inserting a delivery catheter such as a deployment catheter into an artery, deploying components of the endoluminal prostheses system in desired locations, providing pre-cannulated guidewires proximate to target branch arteries, tracking pre-curved angiographic catheters over the pre-cannulated guidewires from a central lumen of a main graft body through fenestrations or other openings in the main graft body and the filling structures, withdrawing the pre-cannulated guidewires, and advancing guidewires through the ostia of the target vessels to cannulate the target vessels, advancing angiographic catheters into the target vessels, withdrawing the guidewires and advancing stiffer guidewires into the target vessels, advancing collapsed support structures over the guidewires into the target vessels, expanding the support structures in the target vessels, inflating balloons to support central lumens of the filling structures, pre-filling the filling structures with a temporary filling medium, verifying the seal and position of the filling structures through angiography, aspirating the temporary filling medium from the filling structures, filling the filling structures with a hardenable filling medium, and verifying the seals of the filling structures through angiography. The steps of the foregoing procedure in accordance with various embodiments can be performed in the sequence described, or can be performed in any suitable sequence, and one or more of the steps may be omitted in various embodiments. In some embodiments, the step of filling the filling structure with the hardenable filling medium is performed with one endoluminal prosthesis before the step of filling the filling structure with the hardenable filling medium is performed with a second endoluminal prosthesis.

Figure 9A:
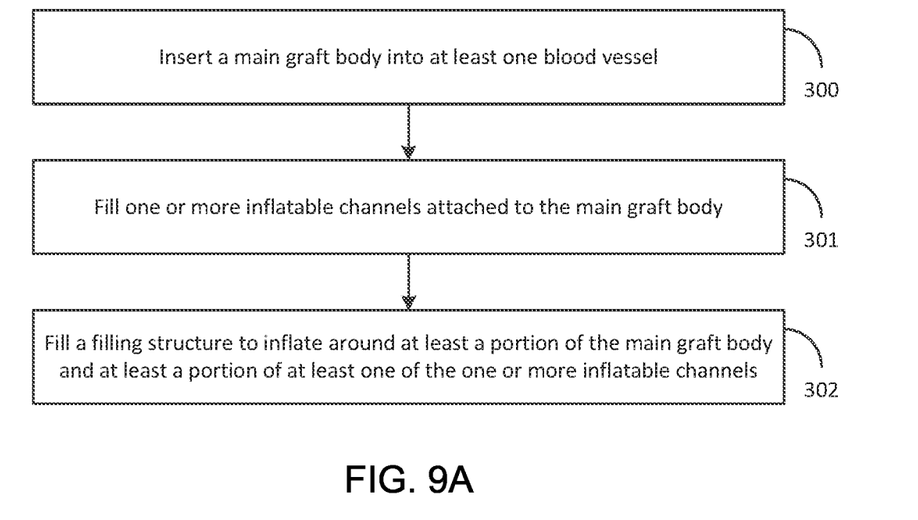
FIG. 9A is a flowchart of a method in accordance with an embodiment for deployment of an endoluminal prosthesis system.

FIG. 9A shows a flowchart of a method in accordance with an embodiment. In step 300, a main graft body is inserted into at least one blood vessel. In step 301, one or more inflatable channels attached to the main graft body are filled. In step 302, a filling structure is filled to inflate around at least a portion of the main graft body and at least a portion of at least one of the one or more inflatable channels. For example, with reference to the endoluminal prosthesis system 20 of FIG. 4, in various embodiments the main graft body 22 is inserted into the aorta 10, the inflatable channels 32A and 32B attached to the main graft body 22 are filled, and the filling structure 26 is filled to inflate around at least a portion of the main graft body 22 and at least a portion of at least one of the one or more inflatable channels 32A and 32B. In some embodiments, the filling structure 26 is attached to the main graft body 22.

Figure 9B:
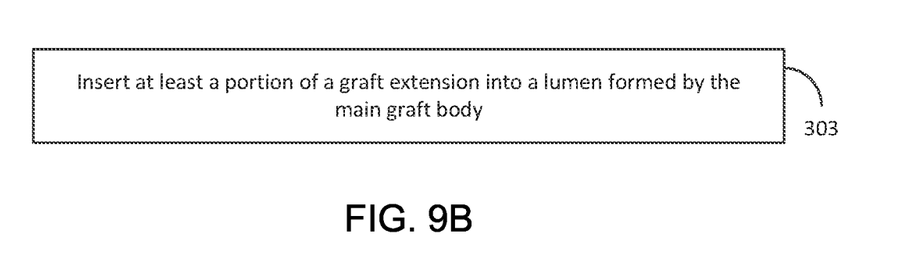
FIG. 9B shows a method in accordance with an embodiment that can be used with the method of FIG. 9A.

FIG. 9B illustrates a method that can be performed along with the method of FIG. 9A. In step 303, at least a portion of a graft extension is inserted into a lumen formed by the main graft body, and the filling structure extends around at least a portion of the graft extension. For example, with reference to the endoluminal prosthesis system 20 of FIG. 4, at least a portion of each of the graft extensions 28 is inserted into the central lumen formed by the main graft body 22, and the filling structure 26 extends around at least a portion of each of the graft extensions 28.

In some embodiments, the filling structure is attached to a graft extension and the method includes inserting at least a portion of the graft extension into a lumen formed by the main graft body. For example, with reference to the endoluminal prosthesis system 50 of FIG. 6, the filling structure 126A is attached to a corresponding one of the graft extensions 28, and at least a portion of the corresponding graft extension 28 has been inserted into the central lumen formed by the main graft body 22.

Figure 9C:
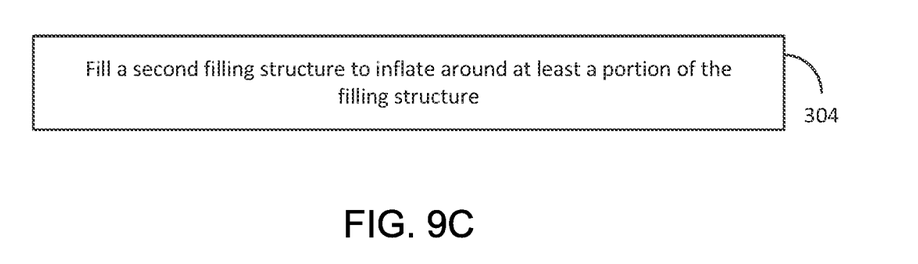
FIG. 9C shows a method in accordance with an embodiment that can be used with the methods of FIGS. 9A and 9B.

FIG. 9C illustrates a method that can be performed along with the methods of FIGS. 9A and 9B. In step 304, a second filling structure is filled to inflate around at least a portion of another filling structure. For example, with reference to the endoluminal prosthesis system 70 of FIG. 7, the filling structure 226A is filled to inflate around at least a portion of the filling structure 226B. Also, the filling structure 226D is filled to inflate around at least a portion of the filling structure 226C.

The order or sequence of any process or method steps may be varied or re-sequenced according to alternative embodiments. Other substitutions, modifications, changes and omissions may also be made in the design, operating conditions, and arrangement of the various exemplary embodiments without departing from the scope of the present invention.

The construction and arrangement of the elements of the endoluminal prostheses systems as shown in the exemplary embodiments are illustrative only. Although embodiments of the present disclosure have been described in detail, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. Some like components have been described in the present disclosure using the same reference numerals in different figures. This should not be construed as an implication that these components are identical in all embodiments; various modifications may be made in various different embodiments. It should be noted that the elements and/or assemblies of the enclosure may be constructed from any of a wide variety of materials that provide sufficient strength or durability, in any of a wide variety of colors, textures, and combinations.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention.

What is claimed is:

1. A system for placement in at least one blood vessel, the system comprising:
   a main graft body;
   one or more inflatable channels attached to the main graft body;
   a separate and distinct graft extension positioned within and axially overlapping a lumen formed by the main graft body; and
   a filling structure having an outer wall and an inner wall, the inner wall defining an inner lumen,
   wherein the filling structure is configured to be filled to form the inner lumen prior to receiving the graft extension, and
   wherein the filling structure is inflatable around at least one portion of the main graft body and at least one portion of at least one of the one or more inflatable channels.

2. The system of claim 1,
   wherein the filling structure is attached to the graft extension.

3. The system of claim 1,
   wherein the filling structure is attached to the graft extension at two or more discrete locations along a length of the graft extension.

4. The system of claim 1,
   wherein the filling structure is attached to the graft extension only at one or more locations that are away from a proximal end of the graft extension; and
   wherein the filling structure is expandable around at least a portion of the proximal end of the graft extension.

5. The system of claim 1, further comprising:
   a second graft extension at least partially insertable into the main graft body.

6. The system of claim 5,
   wherein the filling structure is attached to the second graft extension.

7. The system of claim 5,
   wherein the filling structure is insertable into the blood vessel separate from the main graft body, the graft extension, and the second graft extension.

8. The system of claim 1,
   wherein the filling structure is expandable to fill a space between a wall of the at least one blood vessel and (i) the at least one portion of the main graft body, (ii) the at least one portion of the at least one of the one or more inflatable channels, and (iii) at least a portion of the graft extension.

9. The system of claim 1,
   wherein the filling structure is attached to the main graft body.

10. The system of claim 9,
    wherein the filling structure is expandable beyond a distal end of the main graft body.

11. The system of claim 9,
    wherein a particular inflatable channel of the one or more inflatable channels is located between a proximal end of the main graft body and a location of attachment of the filling structure to the main graft body.

12. The system of claim 11,
wherein a second particular inflatable channel of the one or more inflatable channels is located between a distal end of the main graft body and the location of attachment of the filling structure to the main graft body.

13. The system of claim 1, further comprising:
a second filling structure inflatable around at least a portion of the filling structure.

14. A method, comprising:
inserting a main graft body into at least one blood vessel;
filling one or more inflatable channels attached to the main graft body;
filling a filling structure to inflate around at least a portion of the main graft body and at least a portion of at least one of the one or more inflatable channels, and to form an inner lumen in the filling structure defined by an inner wall and an outer wall of the filling structure; and
inserting at least a portion of a graft extension that is separate and distinct from the main graft body into the filling structure inner lumen to axially overlap said lumen.

15. The method of claim 14,
wherein the filling structure is attached to the main graft body.

16. The method of claim 14, further comprising:
inserting at least a portion of the graft extension into a lumen formed by the main graft body;
wherein the filling structure extends around at least a portion of the graft extension.

17. The method of claim 14,
wherein the filling structure is attached to a graft extension; and
wherein the method further comprises inserting at least a portion of the graft extension into a lumen formed by the main graft body.

18. The method of claim 14, further comprising:
filling a second filling structure to inflate around at least a portion of the filling structure.

19. The system of claim 1, wherein the graft extension is a stent-graft.

20. A system for placement in at least one blood vessel, the system comprising:
a main graft body;
one or more inflatable channels attached to the main graft body;
a separate and distinct graft extension at positioned within and axially overlapping a lumen formed by the main graft body; and
a filling structure having an outer wall and an inner wall, the inner wall defining an inner lumen,
wherein the filling structure integrally formed with the main graft body such that the main graft body forms at least a portion of the inner wall of the filling structure;
wherein the filling structure is inflatable around at least one portion of the main graft body and at least one portion of at least one of the one or more inflatable channels,
wherein the filling structure is configured to be filled to form the inner lumen prior to receiving the graft extension.

* * * * *